United States Patent [19] [11] 3,960,139
Bailey [45] June 1, 1976

[54] SYRINGE DEVICE WITH MEANS FOR REMOVING CONTAMINATES WHEN DRAWING BLOOD SAMPLE

[76] Inventor: Donald L. Bailey, 11018 Muriel Place, Thornton, Colo. 80233

[22] Filed: Jan. 15, 1975

[21] Appl. No.: 541,150

[52] U.S. Cl. ........................... 128/2 F; 128/DIG. 5; 128/218 P; 128/220
[51] Int. Cl.² ......................................... A61B 5/14
[58] Field of Search ............... 128/2 F, 2 G, DIG. 5, 128/218 R, 218 P, 218 M, 218 PA, 218 C, 220, 221, 234; 222/386; 73/425.4 P

[56] References Cited
UNITED STATES PATENTS

| | | | |
|---|---|---|---|
| 2,515,956 | 7/1950 | Greenberg | 128/220 |
| 3,660,033 | 5/1972 | Schwartz | 23/230 B X |
| 3,660,037 | 5/1972 | Sokol | 23/253 R |
| 3,701,434 | 10/1972 | Moore | 128/2 F |
| 3,734,079 | 5/1973 | Weber | 128/2 G |
| 3,748,909 | 7/1973 | Kuo | 73/425.4 P |
| 3,809,298 | 5/1974 | Harris et al. | 222/386 |
| 3,814,079 | 6/1974 | LeRoy | 128/2 F |
| 3,835,835 | 9/1974 | Thompson et al. | 128/2 F |

*Primary Examiner*—Kyle L. Howell
*Attorney, Agent, or Firm*—Burton, Crandell & Polumbus

[57] ABSTRACT

A syringe for taking blood samples includes a tubular body having a main plunger slidably received therein in fluid tight relationship. The tubular body has an opening through the leading end in communication with connection means for receiving a hypodermic needle or the like. The main plunger has a passage there-through in communication with the opening in the leading end of the tubular body and an auxiliary plunger is slidably received in said passage to assist in initially drawing blood into said passage to purge gaseous materials from the opening in the leading end of the tubular body before blood is allowed to flow into the internal chamber of the tubular body.

6 Claims, 3 Drawing Figures

U.S. Patent   June 1, 1976   3,960,139
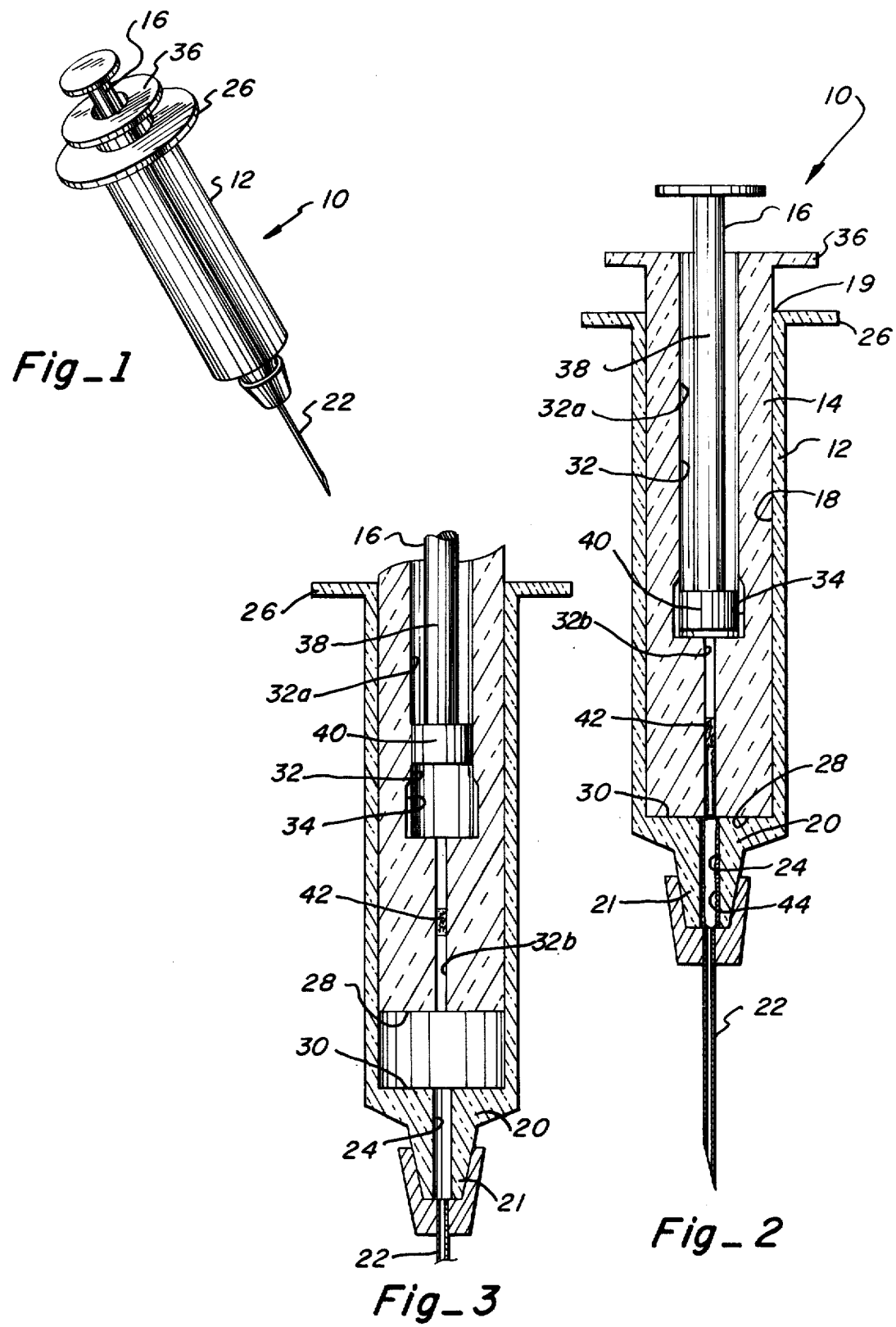
Fig_1
Fig_2
Fig_3

SYRINGE DEVICE WITH MEANS FOR REMOVING CONTAMINATES WHEN DRAWING BLOOD SAMPLE

BACKGROUND OF THE INVENTION

In blood gas analysis, it is important that air and other gaseous materials not be allowed to contaminate the blood as these contaminates distort the results of the gas analysis. Accordingly, prior art syringes adapted to withdraw blood samples from donors are normally preconditioned by the addition of an anticoagulant solution to fill the void or dead space in the syringe and needle, to purge the syringe and needle of air or other gaseous materials and to provide an anticoagulant for the blood. The anticoagulant solution, however, is typically very dilute with the anticoagulant concentration being approximately 1000 units per millileter and the diluent being made up of alcohol, water, and other materials which can also distort the gas analysis of the blood.

Therefore, it is desirable in taking blood samples for blood gas analysis to isolate the blood from extraneous gaseous materials and from the diluent of the anticoagulant solution while leaving the anticoagulant itself to prevent coagulation of the blood.

Accordingly, it is an object of the present invention to provide a new and improved syringe for taking blood samples which prevents contamination by extraneous gases as well as the diluent of anticoagulant solutions.

It is another object of the present invention to provide a syringe for taking blood from a donor wherein the syringe includes a plunger member into which an initial sample of the blood is drawn to purge air and other gaseous materials from the chamber in the syringe thereby preventing the gaseous materials from contaminating the blood sample.

SUMMARY OF THE INVENTION

The syringe of the present invention includes a main tubular body which slidably receives a main plunger in sealed relationship therewith. The leading end of the tubular body includes an opening in communication with a connection element adapted to receive a hypodermic needle or the like through which blood can pass into the chamber defined by the tubular body. The main plunger has a longitudinal passage therethrough communicating at its leading end with the opening in the leading end of the tubular body and an auxiliary plunger is slidably receivable in said passage so as to selectively allow or inhibit the flow of blood into the passage from the opening in the leading end of the tubular body. To assist in this regard, a filter, one-way valve, self-sealing insert or the like is preferably provided in the passage to block the flow of blood in the passage once the blood has passed into the filter or the like.

The syringe is effective in purging air or other gaseous materials from the chamber into which the blood is to be drawn to prevent these gaseous materials from distorting the gas analysis which is later performed on the blood sample. Also, the walls of the passage through which the blood flows into the device can be coated with a dried anticoagulant prior to drawing a blood sample to prevent the blood from coagulating in the syringe and to avoid the use of liquid anticoagulants which also contain diluent components which can distort the blood gas analysis.

BRIEF DESCRIPTION OF THE DRAWINGS

FIG. 1 is a perspective view of the syringe of the present invention.

FIG. 2 is a longitudinal section taken through the syringe of FIG. 1.

FIG. 3 is a fragmentary longitudinal section similar to FIG. 2 with the component parts of the syringe in a different position.

DESCRIPTION OF THE PREFERRED EMBODIMENTS

Referring first to FIG. 1, the syringe 10 of the present invention can be seen to include a housing or tubular body 12, a main plunger member 14 slidably received in the tubular body 12 and an auxiliary plunger member 16 slidably received in the main plunger 14.

The tubular body 12 is of circular transverse cross section and defines an internal chamber 18 into which blood samples are ultimately drawn. The trailing end 19 of the tubular body is open to receive the main plunger 14 and the leading end 20 of the tubular body has a central forward axial extension 21 of frustoconical configuration adapted to receive a hypodermic needle 22 or the like for transmitting blood samples from a donor's artery to the syringe. A passage 24 extends through the leading end 20 of the tubular body and the frustoconical extension 21 to provide communication between the needle and the internal chamber 18 of the tubular body. The tubular body has an outwardly directed annular flange 26 around its trailing end to assist manipulation of the syringe.

The main plunger 14 as mentioned previously, is slidably receivable in the internal chamber 18 of the main tubular body 12 and forms a fluid tight seal therewith. The main plunger is generally of cylindrical configuration with the end 28 being flat and adapted to seat in sealed relationship against the flat inner wall 30 of the leading end of the tubular body for a reason which will become more clear hereinafter. The main plunger has an axial centrally located passage 32 therethrough which is of circular transverse cross section. The passage includes a large diameter portion 32a at the trailing end which extends slightly over half the length of the main plunger and a reduced or smaller diameter portion 32b at the leading end which is in alignment and fluid communication with the passage 24 through the leading end of the tubular body. At the leading end of the large diameter portion 32a of the passage 32, an annular notch 34 is provided in the cylindrical wall of the passage to provide a by-pass which cooperates with the auxiliary plunger 16 in a manner to be described later. Similar to the tubular body, the main plunger has an outwardly directed flange 36 around its trailing end to facilitate manipulation of the syringe.

The auxiliary plunger 16 has a shaft portion 38 of cylindrical configuration and a leading head 40 which is also of cylindrical configuration but enlarged relative to the shaft so as to form a fluid tight sliding seal with the walls of the large diameter portion 32a of the passage 32 in the main plunger 14. The leading head 40 is shorter in length than the annular notch 34 cut in the inner wall of the passage 32 so that when the leading head is aligned with the annular notch, as seen in FIG. 2, fluid is allowed to flow around the head and is not sealed by the engagement of the head with the inner wall of the passage. However, when the leading head is not aligned with the notch, such as when it has been slid in a rearward direction so that the head sealingly engages the walls of the passage 32, fluid is prevented from passing around the head. Further, sliding movement of the auxiliary plunger in a rearward direction creates a low pressure in the leading end of the passage 32 to selectively assist in drawing blood into the syringe.

Positioned within the small diameter portion 32b of the passage 32 in the main plunger 14, is a gas permeable filter 42 adapted to at least partially and preferably totally restrict the flow of blood through the passage 32 both in a forward and rearward direction. The filter could be in the form of a fibrous material, a one way valve, self-sealing insert or the like, but is preferably an absorbent material which expands upon contact with blood to substantially prevent the flow of blood therethrough.

With the exception of the filter 32, the syringe 10 is made of a sterilizable material so that it can be sterilized before use, and preferably the material is economical so that the syringe can be disposed of after use.

In operation of the syringe, in dealing with patients having normal blood pressures, a dilute solution of an anticoagulant, such as heparin, is drawn into the passage 24 through the leading end 20 of the tubular body 12 and usually will flow at least partially into the small diameter portion 32b of the passage 32 in the main plunger 14 with the main plunger being seated in sealed relationship against the inner wall 30 of the tubular body and without the hypodermic needle connected to the syringe. The solution of anticoagulant is allowed to evaporate leaving the dried anticoagulant as a precipitate coating 44 on the internal walls of both the passage 24 through the leading end of the tubular body and the small diameter portion 32b of the passage 32 in the main plunger which was exposed to the anticoagulant, FIG. 2. This process can be quickened by heating the syringe with the anticoagulant solution therein at a selected temperature for a predetermined period of time. After the passages 24 and 32b have been coated with the dried anticoagulant material, the needle 22 is attached to the frustoconical extension 21 and inserted into the artery of the donor patient where the blood pressure of the patient will pump the blood through the needle, through the passage 24 in the leading end of the tubular body, and subsequently into the small diameter portion 32b of the passage in the main plunger until it encounters the filter 42 which thereafter restricts the flow of blood. Of course, for the blood to be pumped into the syringe in this manner, it is important that the auxiliary plunger 16 be positioned so that the leading head 40 is in alignment with the annular notch 34 so that air which previously occupied the passages 24 and 32b in the leading end of the tubular body and in the small diameter portion of the passage in the main plunger respectively, is purged therefrom by the blood as it is admitted. Further, it is important that the main plunger 14 be sealingly seated against the leading end wall 30 of the main tubular to prevent air from flowing radially into a gap at the leading end of the syringe and being trapped there where it can later distort the blood gas analysis of the blood sample drawn into the syringe. After the blood sample has encountered the filter, the auxiliary plunger 16 is slid rearwardly until it seals the large diameter portion 32a of the passage through the main plunger so that the pressure of the blood now entering the syringe, being restricted both by the filter and by the sealed relationship of the auxiliary plunger with the passage through the main plunger, lifts the main plunger and allows the blood to fill the internal chamber 18 of the tubular body until the desired blood sample has been drawn. It will be appreciated that the blood sample drawn will not have contaminating gases such as air therein since the air was purged from the space into which the blood was drawn by the initial flow of the blood. Further, since the anticoagulant was dried prior to drawing the blood sample, the diluent material which normally accompanies anticoagulant solutions cannot distort or otherwise contaminate the blood solution for purposes of blood gas analysis.

When the syringe 10 is used on a donor having an extremely low blood pressure which is insufficient to pump the blood into the syringe, the main and auxiliary plungers are used to draw the blood into the syringe. After the syringe has been coated with the dry anticoagulant material, as in the previously described operation relative to donors with higher blood pressures, the needle is inserted into the artery of the patient and the auxiliary plunger 16 is withdrawn to lower the pressure at the leading end of the syringe so that blood will be attracted and thereby drawn through the needle into the passage 24 through the leading end of the tubular body and into the small diameter portion 32b of the passage 32 through the main plunger 14. Once the blood encounters the filter 42, the filter will prevent the further flow of blood therethrough and with the auxiliary plunger 16 in sealed relationship with the large diameter portion 32a of the passage 32 through the main plunger, the main plunger can then be withdrawn or slid axially in a rearward direction to create a low pressure zone within the internal chamber 18 of the tubular body at the leading end thereof and thereby draw blood into the internal chamber until the desired sample has been drawn. This sample will be free of contaminates, such as air and diluent components of typical liquid anticoagulant solutions, so that the blood gas analysis performed on the blood sample will be accurate and not distorted by the contaminates.

Although the present invention has been described with a certain degree of particularity, it is understood that the present disclosure has been made by way of example and that changes in details of structure may be made without departing from the spirit thereof.

What is claimed is:
1. A syringe for drawing blood comprising:
a tubular body having a leading end with an opening therethrough and connection means in communication with said opening at said leading end for connection to a needle adapted to be inserted into a donor's blood vessel to transfer blood from the blood vessel to the tubular body, and an open trailing end,
a needle connected to said tubular body by said connection means,
a first slide member slidably received in said tubular body in fluid tight relationship therewith, said first slide member having a passage therethrough in communication with said opening in the leading end of the tubular body, and
a second slide member slidably received in said passage in the first slide member in fluid tight relationship therewith, said second slide member having a relatively large portion being in fluid tight relationship with at least a portion of said passage in the first slide member, said passage having a notch in the inner wall thereof at the leading end of said portion of the passage in which the second slide member is disposed, said notch extending along a greater length of the passage than the large portion of the second slide member whereby when the large portion of the second slide member is aligned with said notch, fluid is allowed to flow through the passage.

2. The syringe of claim 1 wherein said passage has a relatively narrow portion extending forwardly from said notch, further including a filter element in said narrow forward portion of the passage, said filter element being adapted to at least partially restrict the flow of liquid therethrough.

3. The syringe of claim 1 further including means on the leading end of the first slide member adapted to establish a fluid tight seal with the leading end of the tubular body when the first slide member is fully inserted into the tubular body.

4. The syringe of claim 3 wherein the leading end of the first slide member and at least the inner surface of the leading end of the tubular body are each flat surfaces.

5. The syringe of claim 1 wherein said notch extends around the entire periphery of the portion of said passage in which said second slide member is disposed.

6. The syringe of claim 1 further including a coating of a dry anticoagulant material on the walls of said opening in the leading end of the tubular body.

* * * * *